United States Patent [19]

Tiller

[11] Patent Number: 4,991,069
[45] Date of Patent: Feb. 5, 1991

[54] END CAP FOR RECHARGEABLE BATTERY INSTRUMENT HANDLE

[75] Inventor: Robert G. Tiller, Auburn, N.Y.

[73] Assignee: Welch Allyn, Inc., Skaneateles Falls, N.Y.

[21] Appl. No.: 525,996

[22] Filed: May 21, 1990

[51] Int. Cl.⁵ .............................................. F21L 11/00
[52] U.S. Cl. ....................................... 362/183; 362/109
[58] Field of Search ............... 362/109, 183, 253, 804; 320/59; 128/801; 351/221

[56] References Cited

U.S. PATENT DOCUMENTS 3,643,083  2/1972  Heine ............................ 362/183 X
4,514,790  4/1985  Will .................................. 362/183

Primary Examiner—Stephen F. Husar
Attorney, Agent, or Firm—Wall and Roehrig

[57] ABSTRACT

An end cap for a rechargeable battery apparatus such as medical diagnostic instruments has a built-in diode arranged in series contact with the rechargeable NiCad battery so that current can flow in the battery charging direction only and the battery can not be discharged by shorting of the charging contact to the case.

9 Claims, 1 Drawing Sheet

END CAP FOR RECHARGEABLE BATTERY INSTRUMENT HANDLE

BACKGROUND OF THE INVENTION

This invention relates to rechargeable battery handles for apparatus, and more particularly medical instrument handles having a rechargeable battery in the handle which is adapted to be inserted into a charger for recharging of the battery when the instrument is not in use.

In recent years diagnostic medical instruments in general, and particularly ophthalmoscopes, otoscopes, retinoscopes, transilluminators and the like, have become smaller and more readily portable by use of small rechargeable batteries placed in the handle of the instrument. The provision of a charger/holding stand in which the instrument may be placed when it is not being used has also become common. This allows much greater flexibility and utilization of the instruments while maintaining them at peak operating condition by automatically charging the battery cell in the handle whenever the instrument is placed in its charging rack.

In order to permit charging of the battery in the instrument handle, one of the contacts of the battery has been allowed to project out of the bottom of the handle so that when it is placed in the charging rack, electrical contact can be made to complete the circuit through the handle for charging of the battery. This unfortunately has also led to a problem with the prior art devices in that as the instruments have become smaller and the doctor's schedule has become more compressed, doctors tend to put the instrument in their pocket when going from one examining room to another. The battery contact being exposed through the bottom of the instrument handle, when the doctor puts the instrument in his pocket, any key, loose change, pencil clip or other metallic object can short the battery contact to the case of the instrument and cause a high current discharge of the battery in the instrument handle.

Not only does this discharge the battery so the instrument is not up to full illumination power when the doctor next tries to use it, but because of the characteristics of the common Nicad rechargeable battery, a very high shorting current is produced which heats up the end of the handle, as well as the coin or the key, as the case may be, to the point that burns can be sustained when one puts their hand on the instrument to remove it from the pocket.

Various suggestions have been put forward as to special switches for disabling the charging circuit, changing the internal connections, not using the case as a conductor, and the like, but all have been rejected because of the lack of convenience and the tendency of the using physician to forget to actuate the charging mechanism when not in use, with the resultant out of service condition of the instrument when the doctor needs it.

OBJECT AND SUMMARY OF THE INVENTION

Accordingly, it is an object of the present invention to provide a rechargeable battery apparatus in which high current short circuit discharge of the battery is prevented.

It is another object of the present invention to provide a pocket type medical instrument such as an ophthalmoscope which overcomes the deficiencies of the prior art.

It is another object of the present invention to provide a pocket instrument having a rechargeable battery in the handle which is impossible to discharge by shorting from the charging battery contact to the case of the instrument.

It is another object of the present invention to provide a rechargeable battery handle closure cap, having a built-in diode, for limiting the flow of electrical current to the charging direction only.

It is a still further object of the present invention to provide an end closure, for an instrument handle having a rechargeable battery therein, with a built-in diode for preventing "short circuit" discharging current while permitting charging current that can be used as a replacement for conventional chargeable battery operated instrument handle end caps.

According to a preferred embodiment of the present invention, I have developed a simple and safe end cap for use with a conventional pocket instrument, such as ophthalmoscopes, having rechargeable batteries in the handle, which includes a built-in diode in the circuit between the battery contact and the external contact for the charging circuit such that when the instrument handle is placed in the charging rack, the battery can be charged by current flowing through the diode into the battery, but when the conductive case of the handle is shorted to the exposed recharging contact, current cannot flow to discharge the battery, even though a coin or the like shorts the charging contact to the case.

BRIEF DESCRIPTION OF THE DRAWINGS

These and other objects of the present invention may be readily examined by reference to the following drawings wherein.

DETAILED DESCRIPTION OF THE PREFERRED EMBODIMENT

Figure 1:
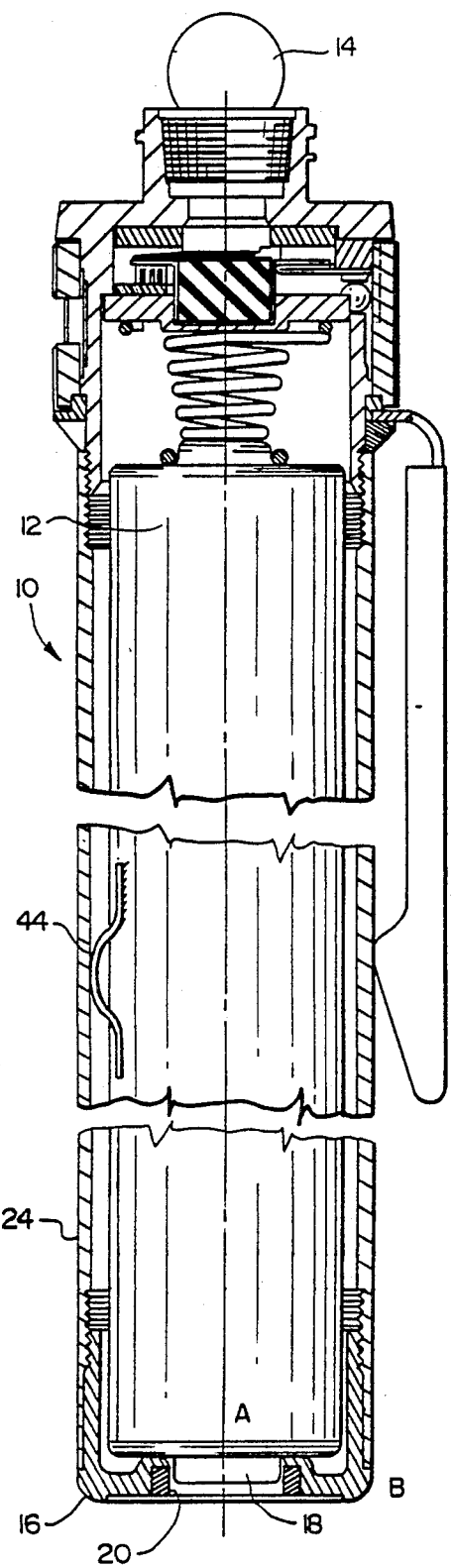
FIG. 1 is a cross sectional view of a typical instrument handle with a rechargeable battery according to the prior art.

Referring now to FIG. 1, there is shown an instrument handle 10 of the type commonly used in ophthalmoscopes, otoscopes, transilluminators, retinoscopes, and the like. A rechargeable Nicad battery pack 12 is commonly mounted therein. A lamp 14 is mounted in the usual socket at one end and an end cap 16 having a central aperture is threadably positioned on the other end.

As may be seen, contact 18 of battery pack 12 extends out through the aperture 20 of cap 16 for contact with the corresponding contact in a charging stand or other charging device. In prior art devices, it was an easy matter to inadvertently short contact 18 to the casing 24 of the handle 10 with a coin or key or the like when the instrument was placed in the doctor's pocket. Because of the characteristics of the Nicad battery, this frequently resulted in a high "short circuit" current which quickly heated the handle and coin to harmful temperature.

Figure 2:
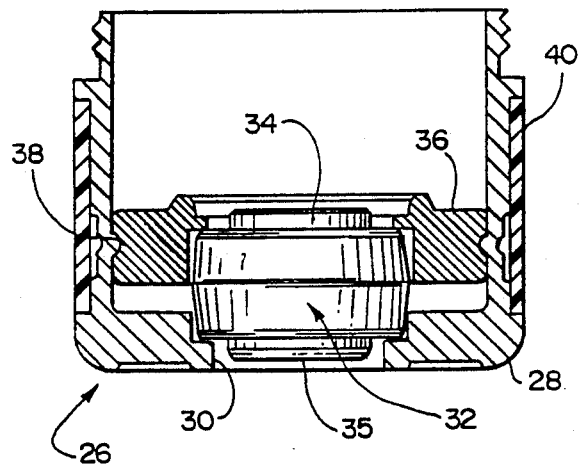
FIG. 2 is a cross sectional view of the end cap of the present invention.

In FIG. 2 there is shown an end cap 26 for use as an end closure of an instrument handle 10 having a rechargeable battery 12. The end cap 26 comprises a cup 28 having an annular hole 30 in the bottom and a cylindrical diode 32 secured therein with the top contact 34 extending upwardly into the battery compartment of handle 10 to contact battery pack 12. Cup 28 is threaded at the upper end to thread into the usual handle end, as shown in FIG. 1, to replace the end cap 16. Other attaching means can obviously be used such as twists or snaps. Diode 32 is secured in cup 28 by an annular ring 36 which is positioned about diode 32 inside cup 28 to axially align it with the opening 30 in the bottom of cup 28. Ring 36 is sized to just fit within the cup 28 and has an annular recess or groove 38 formed in the circumference. After installation ring 36 is fixed in cup 28 by staking or deforming the wall of cup 28 into the recess 38. After securing the diode and ring within the cup 28 a decorative sleeve 40 is placed over the outer surface of the cup 28.

Mounted in this fashion, diode 32 will contact the battery pack 12 through contact 34 and battery contact 18. Charging voltage is applied by the charger through contact 35 just as it used to be applied to contact 18 when the instrument was placed in a charging stand.

Figure 3:
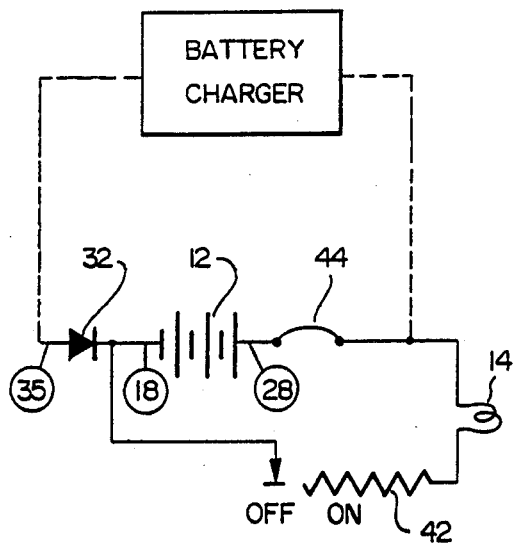
FIG. 3 is a schematic diagram of an instrument handle incorporating the present invention.

As is shown in FIG. 3, the diode 32 is arranged so as to conduct current in the direction for charging rechargeable battery pack 12 while blocking conduction of current in the opposite direction such as would occur upon shorting contact 35 to the cup 28. In the prior art, contact 18 was shorted to case 16. With the cap 26 of FIG. 3, shorting of contact 35 to the case 28 will not produce a "short circuit" current and contact 18 is totally shielded from unwanted shorting contact.

Normal operation of the switch rheostat 42 to the on position will cause current to flow from positive contact of battery 12 through switch/rheostat 42, through the filament of light 14 to the base thereof and thence through the handle case and through spring contact 44 to the negative side of battery 12. Contact 44 is connected internally of the battery pack 12 to the negative side of the Nicad cell. Recharging is accomplished by standing the handle in the usual charger stand so that contact 35 of diode 32 is positioned in electrical contact with the positive side of the charger and the casing at 46 contacts the negative side of the charging circuit. Current will thus flow through diode 32, contact 34, and battery contact 18 to recharge the battery 12 and then back to the other side of the charger completing the charging circuit.

The charger is shown in FIG. 3 in dotted lines to show it is not an integral part of the rechargeable battery handle.

Diode 32 is thus in the charging circuit for battery 12 and also in the discharge circuit to the case in current blocking mode which prevents the unwanted discharging of the battery 12. Diode 32 is not in the circuit for energizing lamp 14 so as to reduce losses and increase battery life.

While we have shown this device as an end cap for a portable rechargeable battery handle for medical diagnostic instruments, it should be understood that a diode button in accordance with the present invention could be inserted in any type of rechargeable battery apparatus as an insert or otherwise secured in the circuit to prevent unwanted discharge of battery 12 upon shorting of the case.

While this invention has been explained with reference to the structure disclosed herein, it is not confined to the details as set forth and this application is intended to cover any modifications and changes as may come within the scope of the following claims.

What is claimed is:

1. An end cap for closure of the end of a rechargeable battery handle for medical diagnostic instruments, such as an ophthalmoscope, which comprises:
   a cup member having, on the open end thereof, means for cooperative attachment to an instrument handle;
   a hole cut in the bottom of the cup member;
   a diode member having anode and cathode contacts;
   said diode being positioned in said cup so that one contact extends out through the hole in the bottom of the cup member and the other extends inwardly in said cup member to contact a battery in the instrument handle when said cup member is attached to an instrument handle.

2. A portable battery powered apparatus of the type having a rechargeable battery positioned for contact with an external charging source comprising in combination:
   a handle member open at one end and having a battery operated device mounted in the other end;
   a rechargeable battery pack having anode contacts at each end, positioned in said handle with one contact in contact with said device and the other contact at the other end adapted to contact an external battery charging source;
   a cap assembly adapted to be mounted on the open end of said handle member to close said end;
   a hole in the end of said cap assembly;
   a diode member mounted in said cap assembly, having a pair of contacts one at each end;
   said diode being positioned with one contact in electrical contact with said rechargeable battery pack anode contact and the other extending through the hole of said cap assembly to contact an external battery charging source to charge said rechargeable battery pack and to prevent short circuit discharge of said battery pack to the case.

3. A device as described in claim 2 wherein a conductive spring member forms an electrical connection between the handle member and the cathode of said rechargeable battery.

4. A device as described in claim 2 wherein the electrical circuits for charging and discharging said battery pack include said diode member connected in series with said rechargeable battery pack to prevent accidental short circuit discharge of said battery by grounding of the exposed anode contact to the handle case while allowing charging.

5. A device as described in claim 2 wherein the electrical circuit for said device includes said rechargeable battery, said spring member, said handle member and a switch/rheostat member all connected in series when said switch/rheostat member is actuated to the on position.

6. An end cap for closure of the open end of a medical instrument battery handle, which comprises:
   a cylindrical cup member, threaded on the open end thereof, for cooperative attachment to a threaded instrument handle;
   a circular hole cut in the bottom of the cup member;
   a cylindrical diode member having cylindrical anode and cathode contacts extending from the bottom and top thereof;

said diode being positioned in said cup so that one contact extends out through the hole in the bottom of the cup member; and an annular ring positioned in said cup about said diode inwardly from the open end thereof to securely position the diode in axial alignment in said hole.

7. A device as described in claim 6 wherein said annular ring has a groove in the outer surface thereof, said cup outer wall is staked into said groove and a decorative sleeve member positioned about the cylindrical surface of said cup to cover said staking area.

8. A device as described in claim 6 wherein said diode is positioned so that the anode contact extends through said hole and the cathode contact is positioned to contact a rechargeable battery positioned in an instrument handle when said cup member is attached to the handle.

9. A medical diagnostic instrument such as an otoscope, ophthalmoscope, retinoscope and the like which comprises a rechargeable battery handle member having an open end;

a battery actuated light mounted in the other end of said handle member;

an end closure for said handle member having a hole in the end thereof;

a rechargeable battery pack having anode contacts at each end positioned in said handle;

a diode member, mounted in said end closure, having a first contact in electrical contact with a battery pack anode and a second contact extending through the hole in said end closure;

whereby when said diode member contact extending through the hole in the end closure is shorted to the case, no short circuit current flows, and when a charger is connected to said contact, the rechargeable battery is recharged.

* * * * *